United States Patent [19]

Brite

[11] Patent Number: 4,461,758

[45] Date of Patent: Jul. 24, 1984

[54] INSECTICIDE INCLUDING POWDERED BORIC ACID

[76] Inventor: Alan D. Brite, 11232 Homedale St., Los Angeles, Calif. 90049

[21] Appl. No.: 24,962

[22] Filed: Mar. 29, 1979

Related U.S. Application Data

[63] Continuation-in-part of Ser. No. 870,740, Jan. 19, 1978, abandoned.

[51] Int. Cl.$^3$ .................. A01N 59/14; G01N 31/00; G01N 31/22; G01N 33/48
[52] U.S. Cl. ........................................ 424/10; 424/148
[58] Field of Search ............................ 424/7, 10, 148

[56] References Cited

U.S. PATENT DOCUMENTS

| | | | |
|---|---|---|---|
| 490,688 | 1/1893 | Smith | 424/148 |
| 1,029,203 | 6/1912 | Loewenthal | 424/148 |
| 1,204,794 | 11/1916 | Levy | 424/10 |
| 1,893,008 | 1/1933 | Wamoscher | 424/10 |
| 2,015,062 | 9/1935 | Benjamin | 424/7 |
| 2,088,651 | 8/1937 | Henninger | 424/7 |
| 3,090,722 | 5/1963 | Baker | 424/7 |

FOREIGN PATENT DOCUMENTS 2021 4/1900 Fed. Rep. of Germany ........ 424/10

OTHER PUBLICATIONS

Chem. Abst. 83,2367n, (1975), Hazebuchi.
Chem. Abst. 63,6265(g), (1965), CIBA Ltd.
The Influence of Repellency on the Efficacy of Blatticides. III. Field Experiments with German Cockroaches with Notes on Three Other Species.

*Primary Examiner*—Douglas W. Robinson
*Attorney, Agent, or Firm*—Lyon & Lyon

[57] ABSTRACT

An insecticide comprising a mixture of powdered boric acid, sucrose octa-acetate or denatonium benzoate, magnesium stearate, silica gel or tricalcium phosphate, and a non-white powdered pigment.

3 Claims, No Drawings

INSECTICIDE INCLUDING POWDERED BORIC ACID

RELATED APPLICATION

This application is a continuation-in-part of my earlier filed U.S. patent application, Ser. No. 870,740 filed Jan. 19, 1978, now abandoned.

DESCRIPTION OF PREFERRED EMBODIMENTS

This invention is directed to the combination of sucrose octa-acetate or Bitrex, a trademarked product composed of denatonium benzoate, and a non-white pigment to a mixture of powdered boric acid and magnesium stearate, silica gel or tricalcium phosphate. It has been found that sucrose octa-acetate is compatible with boric acid powder. Further, it has been found that sucrose octa-acetate when combined with boric acid and magnesium stearate, silica gel or tricalcium phosphate does not render the mixture hydrophilic. It is most important that the mixture not have an affinity for water, which renders a composition ineffective where the humidity may reach high levels for example, as the addition of water to the combination causes the mixture to cake after it has dried out and thereby substantially diminish its effectiveness.

Preferably, the insecticide mixture comprises at least 95% by weight boric acid, less than 5% by weight of a member selected from the group of magnesium stearate, silica gel or tricalcium phosphate, and sucrose octa-acetate or Bitrex and powdered pigment concentrations of less than 1% by weight. Further, it is preferred that the powdered pigment be of a blue color and that the boric acid have a particle size of approximately 100 to 400 mesh.

The blue color of the pigment helps to prevent inadvertent consumption of the insecticide of this invention as it distinguishes the insecticide from common household food items such as flour, sugar or salt. Sucrose octa-acetate and Bitrex while not diminishing the effectiveness of the insecticide have been found to exhibit a taste which is repulsive to humans or domestic animals thereby preventing inadvertent consumption of a quantity of insecticide which would render harm.

Having described this invention in detail, it is understood that modification obvious to those skilled in the art may be made to this invention without the prior art and the scope of the appended claims which follow.

I claim:

1. An insecticidal composition comprising a mixture of at least 95% by weight powdered boric acid, about 5% by weight of a member selected from the group consisting of silica gel, tricalcium phosphate and magnesium sterate, about 1% by weight of denatonium benzoate or sucrose octa-acetate and about 1% by weight of a powdered white pigment.

2. The insecticide claimed in claim 1 wherein said powdered pigment is blue.

3. The insecticide claimed in claim 1 wherein said boric acid is further defined as having a particle size of approximately 100 to 400 mesh.

* * * * *

UNITED STATES PATENT AND TRADEMARK OFFICE
CERTIFICATE OF CORRECTION

PATENT NO. : 4,461,758
DATED : July 24, 1984
INVENTOR(S) : Alan D. Brite

It is certified that error appears in the above-identified patent and that said Letters Patent is hereby corrected as shown below:

Claim 1, line 26, the word "white" should be deleted and the word -- non-white -- inserted therefore.

Signed and Sealed this

Twentieth Day of August 1985

[SEAL]

Attest:

DONALD J. QUIGG

Attesting Officer    Acting Commissioner of Patents and Trademarks